US010587793B2

(12) United States Patent
Yoshino

(10) Patent No.: US 10,587,793 B2
(45) Date of Patent: Mar. 10, 2020

(54) FOCUS CONTROL DEVICE, IMAGING DEVICE, ENDOSCOPE SYSTEM, AND METHOD FOR CONTROLLING FOCUS CONTROL DEVICE

(71) Applicant: OLYMPUS CORPORATION, Tokyo (JP)

(72) Inventor: Koichiro Yoshino, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 214 days.

(21) Appl. No.: 15/705,329

(22) Filed: Sep. 15, 2017

(65) Prior Publication Data
US 2018/0007256 A1 Jan. 4, 2018

Related U.S. Application Data

(63) Continuation of application No. PCT/JP2015/057789, filed on Mar. 17, 2015.

(51) Int. Cl.
H04N 5/232 (2006.01)
H04N 5/235 (2006.01)
(Continued)

(52) U.S. Cl.
CPC ........... H04N 5/23212 (2013.01); A61B 1/04 (2013.01); A61B 1/06 (2013.01); G02B 7/28 (2013.01);
(Continued)

(58) Field of Classification Search
CPC ............. H04N 5/23212; H04N 5/2351; H04N 5/2256; H04N 2005/2255; G02B 7/38;
(Continued)

(56) References Cited

U.S. PATENT DOCUMENTS

2013/0083180 A1* 4/2013 Sasaki ............... H04N 5/23212
348/65
2013/0107107 A1* 5/2013 Ohbuchi ................. G02B 7/38
348/349
2013/0201386 A1 8/2013 Ohbuchi et al.

FOREIGN PATENT DOCUMENTS

CN 103248812 A 8/2013
JP H08-321985 A 12/1996
(Continued)

OTHER PUBLICATIONS

International Search Report dated Jun. 23, 2015 issued in PCT/JP2015/057789.
(Continued)

Primary Examiner — Mulugeta Mengesha
Assistant Examiner — Alazar Tilahun
(74) Attorney, Agent, or Firm — Scully, Scott, Murphy & Presser, P.C.

(57) ABSTRACT

A focus control device includes a processor including hardware, the processor being configured to implement: an area setting process that sets a plurality of areas, each including a plurality of pixels, on a captured image acquired by an imaging section, an evaluation value calculation process that calculates an AF (Autofocus) evaluation value for each of the plurality of set areas, a bright spot influence rate calculation process that calculates a bright spot influence rate for each of the plurality of set areas, based on whether or not the area includes a high luminance portion determined to have a size equal to or larger than a given size, and focus control based on the AF evaluation value and the bright spot influence rate.

10 Claims, 11 Drawing Sheets

(51) Int. Cl.
*H04N 5/225* (2006.01)
*A61B 1/06* (2006.01)
*A61B 1/04* (2006.01)
*A61B 1/00* (2006.01)
*G03B 13/36* (2006.01)
*G02B 7/36* (2006.01)
*G02B 7/28* (2006.01)
*G02B 23/24* (2006.01)
*G02B 7/38* (2006.01)

(52) U.S. Cl.
CPC .................. *G02B 7/36* (2013.01); *G02B 7/38* (2013.01); *G02B 23/2461* (2013.01); *G03B 13/36* (2013.01); *H04N 5/2256* (2013.01); *H04N 5/2351* (2013.01); *A61B 1/00009* (2013.01); *A61B 1/00188* (2013.01); *H04N 2005/2255* (2013.01)

(58) Field of Classification Search
CPC ........ G02B 23/2461; G02B 7/28; G02B 7/36; A61B 1/06; A61B 1/04; A61B 1/00009; A61B 1/00188; G03B 13/36
See application file for complete search history.

(56) References Cited

FOREIGN PATENT DOCUMENTS

| | | |
|---|---|---|
| JP | 2004-294788 A | 10/2004 |
| JP | 2004-309653 A | 11/2004 |
| JP | 2013-097082 A | 5/2013 |
| JP | 2013-148678 A | 8/2013 |

OTHER PUBLICATIONS

Chinese Office Action dated Jun. 5, 2019 received in Chinese Patent Application No. 201580077807.8.

* cited by examiner

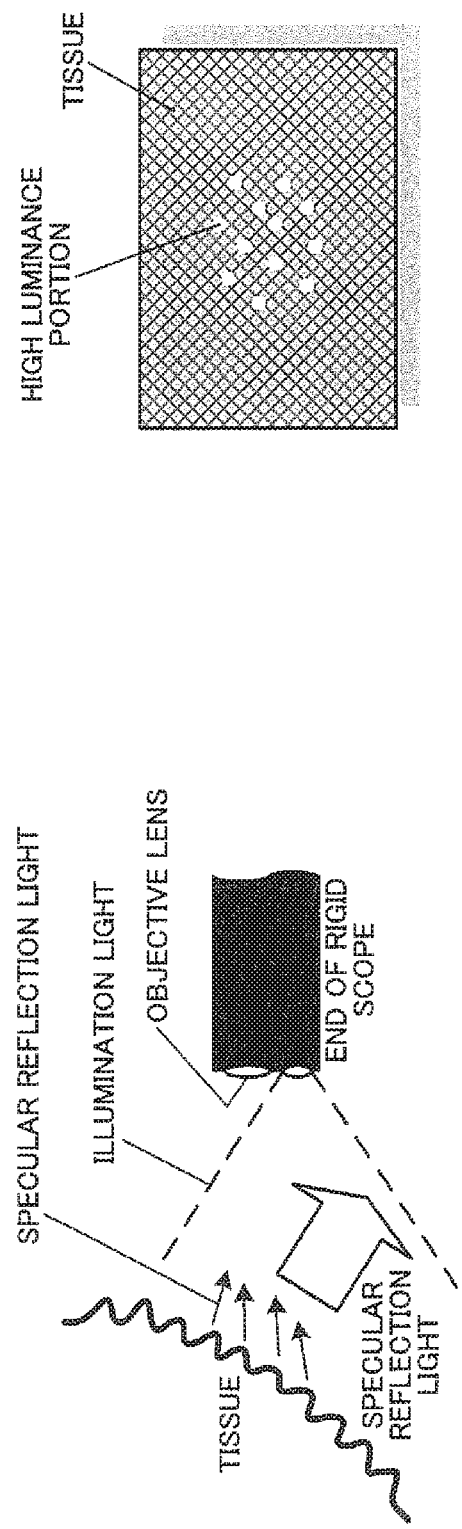

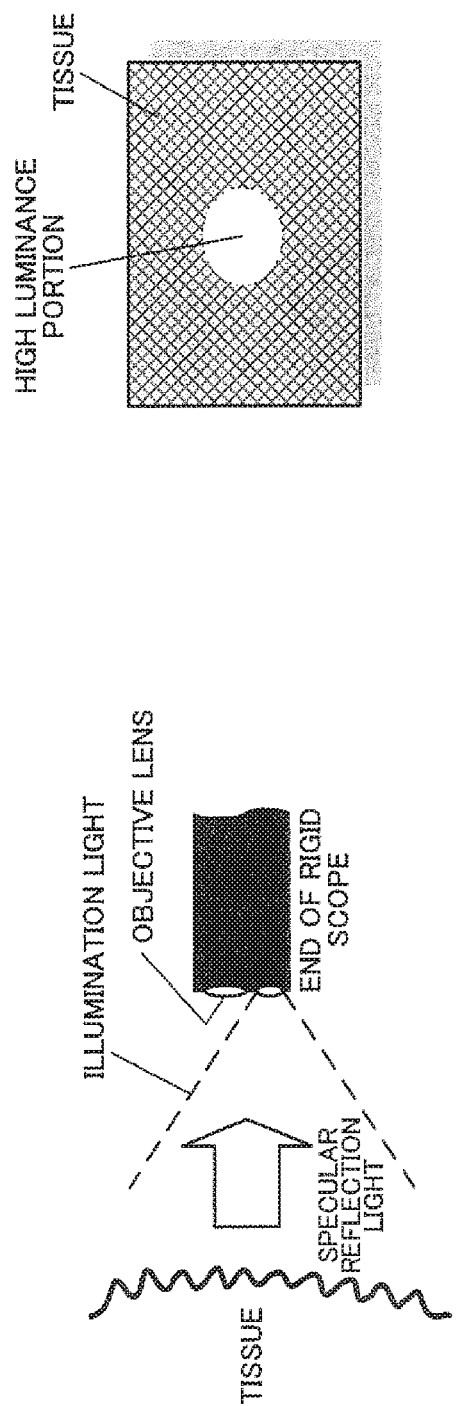

BRIGHT SPOT INFLUENCE
RATE CALCULATION MASK

HIGH LUMINANCE PIXEL
DETERMINATION RESULT

FOCUS CONTROL DEVICE, IMAGING DEVICE, ENDOSCOPE SYSTEM, AND METHOD FOR CONTROLLING FOCUS CONTROL DEVICE

CROSS REFERENCE TO RELATED APPLICATION

This application is a continuation of International Patent Application No. PCT/JP2015/057789, having an international filing date of Mar. 17, 2015, which designated the United States, the entirety of which is incorporated herein by reference.

BACKGROUND

A depth of field as deep as possible is required for an endoscope system so that the user can easily perform diagnosis and treatment. In recent years, the depth of field of an endoscope system has become shallow along with the use of an image sensor having a large number of pixels, and an endoscope system that performs an autofocus (AF) function has been proposed.

In the endoscope system, tissue is irradiated with illumination light emitted from an illumination section, and an image is acquired as a result of focusing resulting reflected light by an objective lens. Generally, in the endoscope system, the illumination section and the objective lens are disposed close to an insert section to be inserted into a body. Thus, light as a result of specular reflection of the illumination light at various positions of the surface of tissue as the object is incident on the objective lens, forming bright spots. As a result, the acquired image includes multiple high luminance portions (saturated portions) of various sizes.

In general contrast AF control, a focus lens position with the largest contrast value is determined to be an in-focus lens position. Unfortunately, when an image includes high luminance portions, the largest contrast value might be achieved at a lens position deviated from the actual in-focus lens position due to an increased edge in the high luminance portions attributable to blurring (as will be described in detail below with reference to FIG. 1A). In the high luminance portions, contrast information on the object is lost due to saturation of a pixel value of the image, and thus the contrast value cannot be accurately calculated. All things considered, the contrast AF control might fail to accurately bring the object into focus when the image includes the high luminance portions.

SUMMARY

According to one aspect of the invention, there is provided a focus control device comprising:
a processor comprising hardware,
the processor being configured to implement:
an area setting process that sets a plurality of areas, each including a plurality of pixels, on a captured image acquired by an imaging section;
an evaluation value calculation process that calculates an AF (Autofocus) evaluation value for each of the plurality of set areas;
a bright spot influence rate calculation process that calculates a bright spot influence rate for each of the plurality of set areas, based on whether or not the area includes a high luminance portion determined to have a size equal to or larger than a given size; and
focus control based on the AF evaluation value and the bright spot influence rate.

According to another aspect of the invention, there is a focus control device comprising:
a processor comprising hardware,
the processor being configured to implement:
an evaluation value calculation process that calculates an AF (Autofocus) evaluation value based on a captured image acquired by an imaging section; and
focus control based on the AF evaluation value,
wherein when a high luminance portion is a group of contiguous high luminance pixels, the processor performs the focus control with contribution of the AF evaluation value calculated based on a pixel other than the high luminance pixel to the focus control set to be first contribution, and with the contribution of the AF evaluation value calculated based on the high luminance portion determined to have a size smaller than a given size to the focus control set to be the first contribution.

According to another aspect of the invention, there is an imaging device comprising:
the above focus control device; and
the imaging section.

According to another aspect of the invention, there is an endoscope system comprising:
the above focus control device; and
an insert section that is inserted into an observation target,
wherein the insert section includes, in an end portion:
an illumination section that emits illumination light; and
the imaging section that acquires the captured image based on reflected light of the illumination light from an object.

According to another aspect of the invention, there is a method for controlling a focus control device, the method comprising:
setting a plurality of areas, each including a plurality of pixels, on a captured image acquired by an imaging section;
calculating an AF (Autofocus) evaluation value for each of the plurality of set areas;
calculating a bright spot influence rate for each of the plurality of set areas, based on whether or not the area includes a high luminance portion determined to have a size equal to or larger than a given size; and
performing focus control based on the AF evaluation value and the bright spot influence rate.

According to another aspect of the invention, there is a method for controlling a focus control device, the method comprising:
calculating an AF (Autofocus) evaluation value based on a captured image acquired by an imaging section; and
performing focus control based on the AF evaluation value,
wherein when a high luminance portion is a group of contiguous high luminance pixels, in the focus control based on the AF evaluation value, the focus control is performed with contribution of the AF evaluation value calculated based on a pixel other than the high luminance pixel to the focus control set to be first contribution, and with the contribution of the AF evaluation value calculated based on the high luminance portion determined to have a size smaller than a given size to the focus control set to be the first contribution.

BRIEF DESCRIPTION OF THE DRAWINGS

FIG. 2A illustrates an example of a positional relationship between an insert section of an endoscope system and tissue, and FIG. 2B is a schematic view of a captured image acquired with the positional relationship illustrated in FIG. 2A.

FIG. 3A illustrates an example of a positional relationship between the insert section of the endoscope system and the tissue, and FIG. 3B is a schematic view of a captured image acquired with the positional relationship illustrated in FIG. 3A.

DESCRIPTION OF EXEMPLARY EMBODIMENTS

Figure 1A:
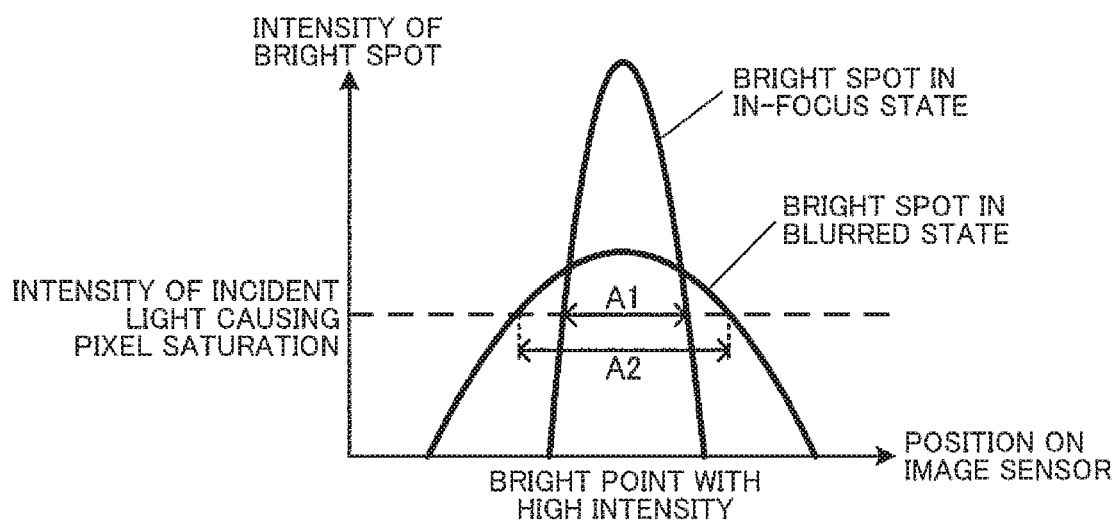
FIG. 1A and FIG. 1B are diagrams illustrating a difference in a size of a high luminance portion between an in-focus state and a blurred state.

According to one embodiment of the invention, there is provided a focus control device comprising:
a processor comprising hardware,
the processor being configured to implement:
an area setting process that sets a plurality of areas, each including a plurality of pixels, on a captured image acquired by an imaging section;
an evaluation value calculation process that calculates an AF (Autofocus) evaluation value for each of the plurality of set areas;
a bright spot influence rate calculation process that calculates a bright spot influence rate for each of the plurality of set areas, based on whether or not the area includes a high luminance portion determined to have a size equal to or larger than a given size; and
focus control based on the AF evaluation value and the bright spot influence rate.

According to another embodiment of the invention, there is a focus control device comprising:
a processor comprising hardware,
the processor being configured to implement:
an evaluation value calculation process that calculates an AF (Autofocus) evaluation value based on a captured image acquired by an imaging section; and
focus control based on the AF evaluation value,
wherein when a high luminance portion is a group of contiguous high luminance pixels, the processor performs the focus control with contribution of the AF evaluation value calculated based on a pixel other than the high luminance pixel to the focus control set to be first contribution, and with the contribution of the AF evaluation value calculated based on the high luminance portion determined to have a size smaller than a given size to the focus control set to be the first contribution.

According to another embodiment of the invention, there is an imaging device comprising:
the above focus control device; and
the imaging section.

According to another embodiment of the invention, there is an endoscope system comprising:
the above focus control device; and
an insert section that is inserted into an observation target,
wherein the insert section includes, in an end portion:
an illumination section that emits illumination light; and
the imaging section that acquires the captured image based on reflected light of the illumination light from an object.

According to another embodiment of the invention, there is a method for controlling a focus control device, the method comprising:
setting a plurality of areas, each including a plurality of pixels, on a captured image acquired by an imaging section;
calculating an AF (Autofocus) evaluation value for each of the plurality of set areas;
calculating a bright spot influence rate for each of the plurality of set areas, based on whether or not the area includes a high luminance portion determined to have a size equal to or larger than a given size; and
performing focus control based on the AF evaluation value and the bright spot influence rate.

According to another embodiment of the invention, there is a method for controlling a focus control device, the method comprising:
calculating an AF (Autofocus) evaluation value based on a captured image acquired by an imaging section; and
performing focus control based on the AF evaluation value,
wherein when a high luminance portion is a group of contiguous high luminance pixels, in the focus control based on the AF evaluation value, the focus control is performed with contribution of the AF evaluation value calculated based on a pixel other than the high luminance pixel to the focus control set to be first contribution, and with the contribution of the AF evaluation value calculated based on the high luminance portion determined to have a size smaller than a given size to the focus control set to be the first contribution.

The exemplary embodiments of the invention are described below. Note that the following exemplary embodiments do not in any way limit the scope of the invention laid out in the claims. Note also that all of the elements described below in connection with the exemplary embodiments should not necessarily be taken as essential elements of the invention.

1. Method

As described above, when a captured image, an AF area used for calculating an AF evaluation value in the captured image in particular, includes a high luminance portion (bright spot), highly accurately AF is disabled due to the effect of the high luminance portion. More specifically, as described below with reference to FIG. 1A, a size of a bright spot is large in a slight blurred (out of focus) state. As a result, the AF evaluation value in the blurred state overwhelms the AF evaluation value in an in-focus state. Thus, in a case of movie AF (continuous AF), a lens is driven in an inappropriate direction due to erroneous determination of an in-focus direction. In still image AF (single AF), the lens is driven to an erroneous position (the out of focus position) due to erroneous determination of the peak of the AF evaluation value.

The bright spot herein indicates a point with a high pixel value (luminance value) as a result of receiving specular reflection light from an object by an imaging section. The high luminance portion, on the other hand, indicates an area in a captured image with a high pixel value, an example of which includes an area in a captured image with a saturated luminance value. In an endoscope system or the like in which a distance between an end of an insert section and an object is short and an image sensor has a high sensitivity (in terms of a luminance value relative to light intensity), when the illumination light has high intensity, or in the other like situations, there will be an area with a high pixel value, which is the high luminance portion herein, regardless of whether light from the object is specular reflection light or diffuse reflection light. Thus, according to the definition of the present embodiment, the bright spot may basically lead to the high luminance portion, but the high luminance portion is not necessarily formed by the bright spot. Still, in processing of implementing focus control according to the present embodiment, clear distinction between the high luminance portion and the bright spot is a low priority. Thus, in the description below, the term "bright spot" is used in a portion where the specular reflection light is clearly involved. In other portions, the "bright spot" and the "high luminance portion" are used with approximately the same definition.

JP-A-2004-294788 and JP-A-8-321985 disclose an attempt to achieve appropriate (accurate) AF by reducing the negative impact of the bright spot. In JP-A-2004-294788, the processing relies on an average luminance in a given area (for example, an evaluation block obtained by subdividing an AF area) or the like. Thus, when a given value is obtained as an average luminance of an area, the value obtained as a result of averaging a high luminance area and a relatively low luminance area and the value obtained with the entire area having an intermediate luminance are not distinguished from each other.

In the processing disclosed in JP-A-8-321985, an area of the high luminance portion in an area is obtained by using a sum of areas of the high luminance portions in the area, for example. Thus, when an area S of the high luminance portion is obtained, the area S obtained as a sum of areas of multiple small bright spots in the captured image and the area S as an area of a single large bright spot in the captured image are not distinguished from each other.

Figure 1B:
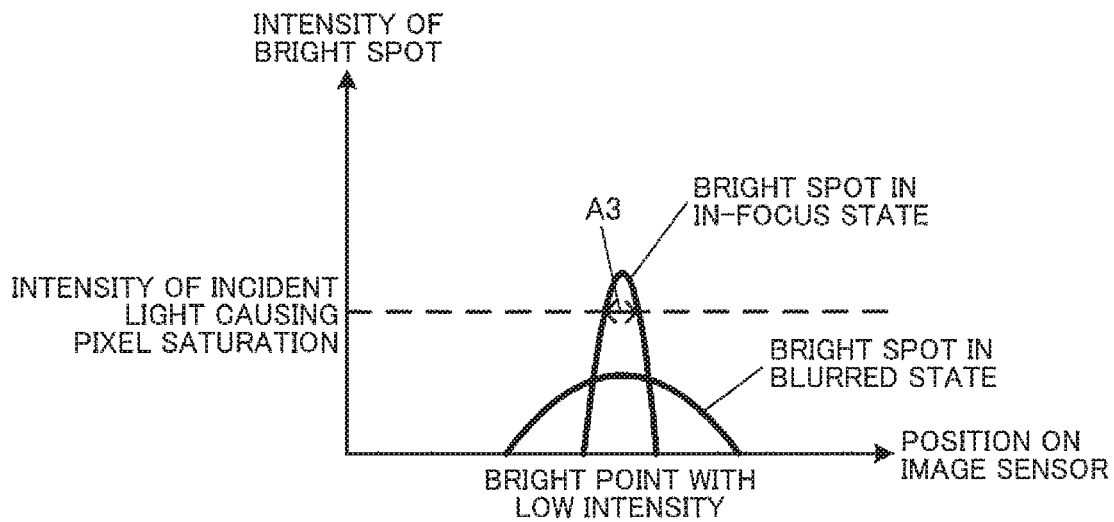

The impact of the bright spot on the AF control is described with reference to FIG. 1A and FIG. 1B. FIG. 1A and FIG. 1B are each a diagram illustrating intensity distributions of a bright spot on the image sensor in an in-focus state and a blurred state. In the figures, a horizontal axis represents a position on the image sensor, and a vertical axis represents an intensity of the bright spot. Here, a saturated pixel range corresponds to the high luminance portion in the image acquired by the image sensor. The high luminance portion is not limited to the area with saturated pixel values (or luminance values), and may be an area with a pixel value higher than a threshold value as a given pixel value.

FIG. 1A and FIG. 1B respectively illustrate a bright spot with a high intensity and a bright spot with a low intensity. As illustrated in FIG. 1A, the bright spot with a high intensity results in a larger area of the high luminance portion in the image in the blurred state compared with a case where tissue as the object is in focus. More specifically, A1<A2 holds true, where A1 represents the size (a length in a direction of the horizontal axis illustrated in FIG. 1A) of the bright spot in the in-focus state and A2 represents the size in the blurred state. Generally, a boundary of the high luminance portion has a higher contrast than the tissue, and thus also has a larger AF evaluation value than the tissue. Thus, when the AF area includes a bright spot with a high intensity, the AF evaluation value is larger in the blurred state than in the state where the object surface is in focus, due to an increase in the length of the boundary of the high luminance portion caused by the blurring. As a result, the AF control relying on the peak AF evaluation value might end in a failure to bring the surface of the tissue into focus.

On the other hand, as illustrated in FIG. 1B, when the bright spot has a low intensity, blurring results in a smaller area of the high luminance portion (or no high luminance portion) in the image. Thus, the AF evaluation value is smaller in the blurred state compared with the state where the object surface is in focus. Specifically, the in-focus state involves the bright spot having a size A3 (>0), whereas the blurred state involves no high luminance portion. Thus, the bright spot with a low intensity as illustrated in FIG. 1B has no negative impact on the AF control.

As described above, only the bright spot with a high intensity has a negative impact on the AF control. Thus, the bright spot with a high intensity needs to be not used in the AF control or used with a smaller contribution to the AF control. On the other hand, the AF control (for example, similarly used as the area that is not the high luminance portion) can be normally performed even when the bright spot with a low intensity is used.

The description with reference to FIG. 1A and FIG. 1B indicates that the bright spots should be handled differently depending on the intensity, and does not mention the size of the bright spot. According the description, a bright spot with a high intensity has a large impact on the AF control even when the size thereof is small, whereas a bright spot with a low intensity has a limited impact on the AF control even when the size thereof is large.

However, the present applicants have found out through research that there are cases where the size and the intensity of the high luminance portion are correlated. An example of such cases includes a case where the AF control is performed with an image captured by an endoscope system or the like.

The relationship between the shape (size) of the high luminance portion and the intensity of the bright spot in an image acquired by the endoscope system is described. FIGS. 2A to 3B illustrate examples of image capturing conditions and the resulting images. An example where an image of tissue inclined relative to an optical axis of the objective lens is captured as illustrated in FIG. 2A is described. Here, in a portion around the optical axis of the objective lens, incident light on the objective lens includes almost no specular reflection light from the surface of the tissue, and mainly includes light after scattering in the tissue. In most cases, the surface of tissue has minute recesses and protrusions, causing only a part of the illumination light reflected toward the objective lens by specular reflection, resulting in bright spots with low intensities. Thus, the resultant image includes multiple small high luminance portions as illustrated in FIG. 2B.

An example where an image of tissue substantially orthogonal to the optical axis of the objective lens is captured as illustrated in FIG. 3A is described. Here, in the portion around the optical axis of the objective lens, the incident light on the objective lens includes specular reflection light as a result of a significant portion of the illumination light being reflected on the surface of tissue, resulting in a bright spot with a high intensity. Thus, the resultant image includes a large high luminance portion as illustrated in FIG. 3B.

Thus, an intensity of a bright spot can be estimated, to some extent, from an area of the high luminance portion in an image acquired by the endoscope system. Specifically, a larger area of the high luminance portion can be estimated to be a bright spot with a higher intensity. Here, the description is given on the portion around the optical axis of the objective lens for simplifying the description. It is to be noted that the same applied to other areas.

Specifically, in a case where the imaging section and the illumination section are positioned close to each other and an optical axis direction of the imaging section and a light emitting direction of the illumination section are close to each other as in the endoscope system or the like, the size of the high luminance portion can be regarded as being correlated with the intensity, as described with reference to FIGS. 2A to 3B.

Specifically, a large high luminance portion in a captured image is estimated to have a high intensity to have a large impact on the AF control. On the other hand, a small high luminance portion in a captured image is estimated to have a low intensity and has a limited impact on the AF control. Thus, appropriate AF control can be achieved by taking the size of the high luminance portion into consideration.

Specifically, a given evaluation block including small bright spots from the AF control has not been used or has been used with small contribution to the AF control performed with the conventional method, depending on the average luminance or an area (total area) of the bright spots. Nonetheless, as described above, information on such an evaluation block is harmless, as long as the evaluation block does not further include large bright spots. Thus, by intentionally ignoring small bright spots (performing the AF control without taking the small bright spots into consideration), the AF evaluation value that has not been used in the conventional method can be appropriately used. As a result, a high AF evaluation value can be acquired as a whole. Thus, even in a situation where the conventional method results in an AF evaluation value that is too low to accurately determine a driving direction of the lens due to heavy blurring, an AF evaluation value of a certain level can be expected to be obtained, whereby the lens can be driven in an appropriate direction and the other like effects can be achieved.

Figure 4:
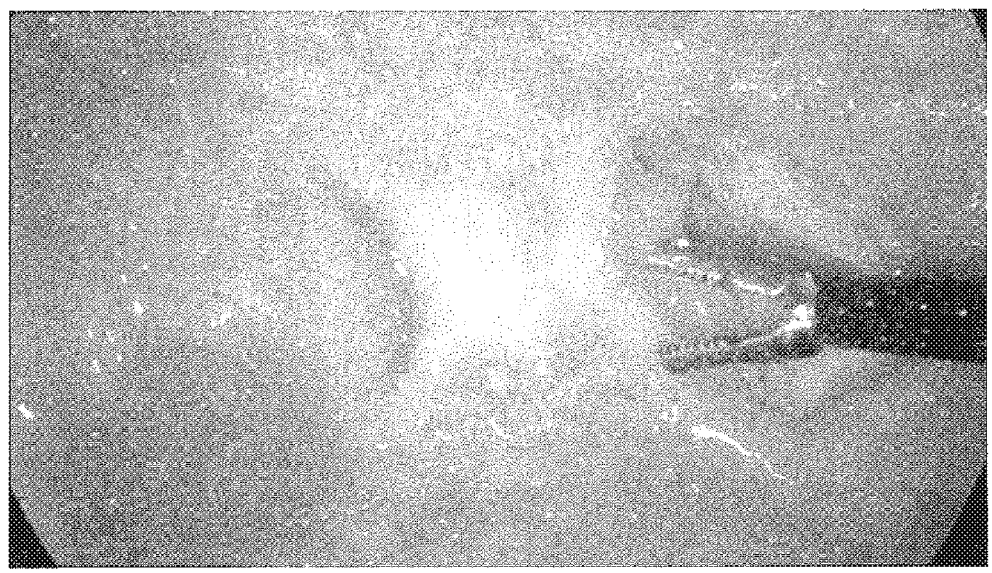
FIG. 4 illustrates an example of a captured image acquired by the endoscope system.

The method according to the present embodiment is particularly effective for a captured image acquired by the endoscope system, that is, an in-vivo image. This is because the endoscope system is likely to capture an image in which small bright spots are distributed over a wide area, because the emitting direction of the illumination section and the optical axis direction of the imaging section are close to each other and because the object is wet in most cases due to body fluid in the tissue or water sending processing in an endoscopic procedure. FIG. 4 illustrates an example of the in-vivo image. In FIG. 4, white portions are the high luminance portions with saturated pixel values. As can be seen in FIG. 4, high luminance portions each having a small area are widely distributed over the entire captured image. Thus, when an evaluation block including small bright spots is set as a null block (a block not used in the AF control), all the evaluation blocks in the AF area are likely to be set as null blocks. It is a matter of course that such a situation results in a failure to execute the AF control, and thus is inappropriate. Thus, the above described configuration does not set the null blocks due to the small bright spots therein, that is, only the bright spots of a given size or larger are omitted from the AF control. Thus, the AF control can be appropriately performed even on a captured image such as that illustrated in FIG. 4.

Figure 5:
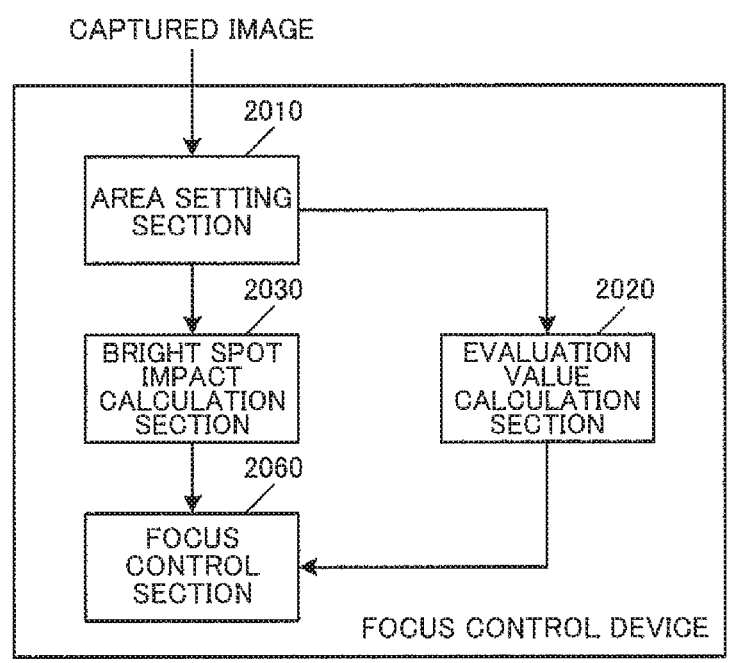
FIG. 5 illustrates a configuration example of a focus control device according to the present embodiment.

In view of the above, the present applicants propose the following focus control device. Specifically, as illustrated in FIG. 5, the focus control device according to the present embodiment includes: an area setting section 2010 that sets a plurality of areas (evaluation blocks), each including a plurality of pixels, on a captured image acquired by an imaging section (an imaging section 200 illustrated in FIG. 6 for example); an evaluation value calculation section 2020 that calculates an AF (Autofocus) evaluation value for each of the plurality of set areas; a bright spot influence rate calculation section 2030 that calculates a bright spot influence rate for each of the plurality of areas thus set, based on whether or not there is a high luminance portion determined to have a size equal to or larger than a given size; and a focus control section 2060 that performs focus control based on the AF evaluation value and the bright spot influence rate. For example, the focus control section 2060 may include an in-focus direction determination section 2040 and a focus lens control section 2050 illustrated in FIG. 8 and described below. As described above, in the processing according to the present embodiment, the bright spot and the high luminance portion need not to be clearly distinguished from each other. Thus, the bright spot influence rate may also be referred to as a high luminance portion impact (high luminance area impact).

The high luminance portion is a group of high luminance pixels that are contiguous. The high luminance pixel is a pixel with a luminance value that is equal to or higher than a threshold value, an example of which includes a saturation value (the largest possible luminance value). As described above, at least one of or a combination of two or more of R, G, and B pixel values may be used instead of the luminance value as described below. The term "contiguous" indicates that a given high luminance pixel is adjacent to other high luminance pixels. Such adjacent pixels may be four pixels on upper, lower, left, and right sides of the pixel of interest, eight pixels surrounding the pixel of interest, or the like.

Here, the given size is a size, on the captured image, corresponding to a bright spot intensity that may affect the AF control. The size may be 3×3 pixels as described below with reference to FIG. 11A, or the other like sizes such as 5×5 pixels. The given size depends on a pitch of pixels on the image sensor, a condition of an imaging optical system, or the like, and thus can be set to various specific values. The given size may not be a fixed value and may be variably set. For example, the focus control device may automatically change the value of the given size based on the condition of the imaging optical system (such as a zoom ratio), or based on an input from a user of the focus control device.

The configuration described above can flexibly perform the AF control in accordance with the size of the high luminance portion. As a result, the object can be accurately brought into focus.

The focus control device according to the present embodiment includes: the evaluation value calculation section 2020 that calculates an AF evaluation value based on the captured image acquired by the imaging section; and the focus control section 2060 that performs the focus control based on the AF evaluation value. When a high luminance portion is a group of contiguous high luminance pixels, the focus control section 2060 can be regarded as performing the focus control with contribution of the AF evaluation value calculated based on a pixel other than the high luminance pixel to the focus control set to be first contribution, and with the contribution of the AF evaluation value calculated based on the high luminance portion determined to have a size smaller than a given size to the focus control set to be the first contribution.

Thus, the high luminance portion smaller than the given size can be treated equally as the pixel that is not the high luminance pixel, that is, an area that is not included in the high luminance portion and thus appropriately reflects the contrast of the object. In this configuration, the focus control section 2060 performs the focus control with the contribution of the AF evaluation value calculated from the high luminance portion determined to have a size equal to or larger than the given size to the focus control set to be second contribution smaller than the first contribution. Thus, the negative impact of the high luminance portion having a size that is equal to or larger than the given size on the AF control is reduced as in the conventional method.

Specifically, an obtained AF evaluation value or the like that has the first contribution is used in the AF control with no particular limitation, and corresponds to weight 1 in a configuration employing weighting described below. The second contribution, which is smaller than the first contribution, may correspond to a weight 0 so that the corresponding AF evaluation value is not completely used, or may correspond to a weight between 0 and 1. Here, the first contribution is used in such a manner that the contribution is not compromised due to the detection of a small high luminance portion. This means that the contribution of the AF evaluation value from a high luminance portion smaller than the given size can be lowered in accordance with a factor other than the high luminance portion (detection of another noise factor for example). Each of the first and the second contributions may not be a single value, and may be a given range of values. Furthermore, each of the first and the second contributions may not be a fixed value and may be variably set.

Thus, the AF control can be performed in accordance with the size of the high luminance portion. All things considered, the AF control can be appropriately performed even in a situation difficult for the conventional method, such as the example illustrated in FIG. 4 where the small bright spots are widely distributed in the AF area.

Figure 6:
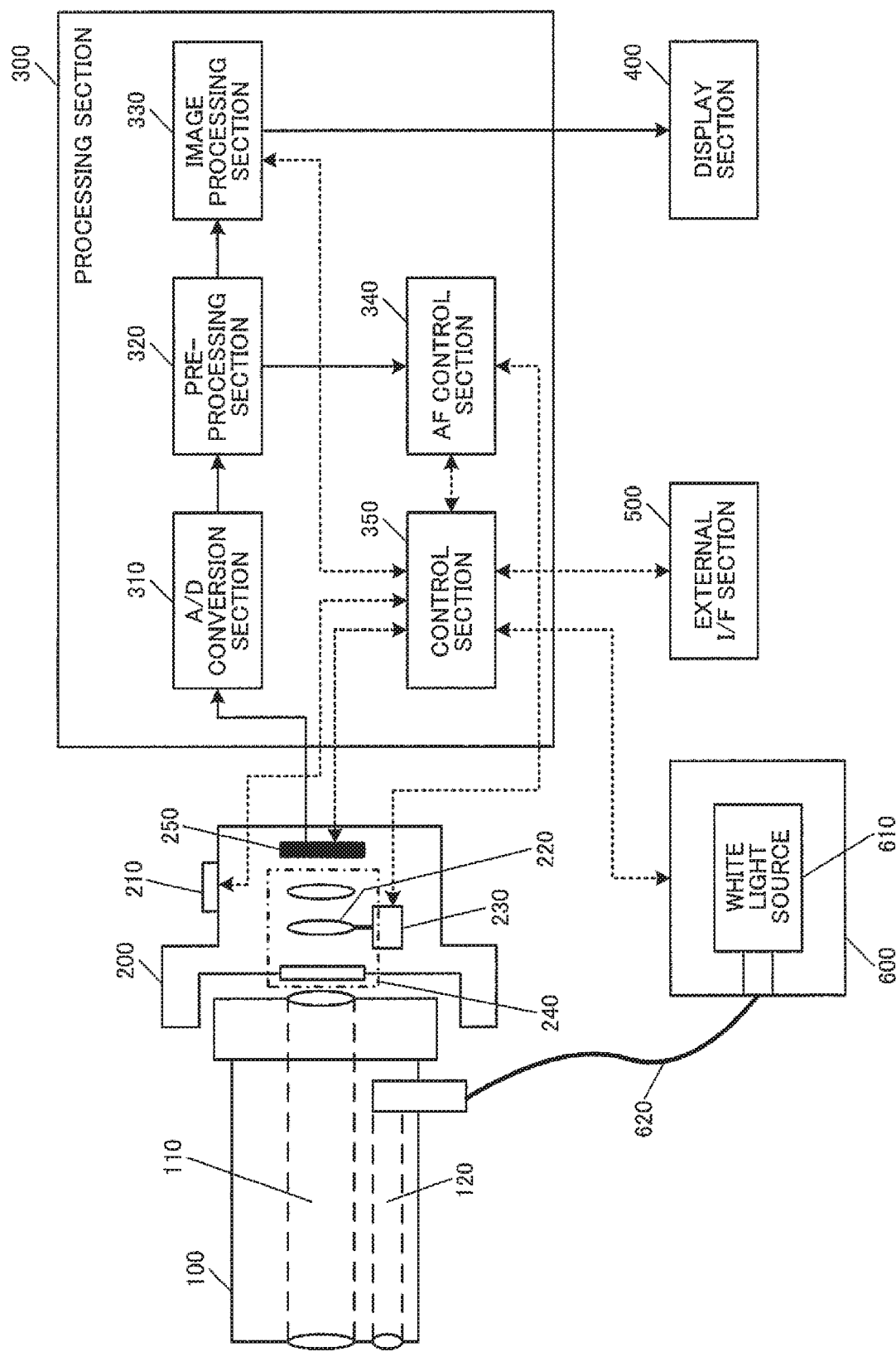
FIG. 6 illustrates a configuration example of an endoscope system according to the present embodiment.

Specifically, the focus control device herein may be a configuration corresponding to a processing section 300 (more specifically, an AF control section 340) in an endoscope system described below with reference to FIG. 6. It is to be noted that the method according to the present embodiment is not limited to the focus control device, and may be applied to an imaging device including the focus control device and the imaging section 200.

Furthermore, the present embodiment may be applied to the endoscope system described below with reference to FIG. 6 that includes a focus control device (processing section 300) and an insert section (rigid scope 100). In such a case, the insert section has an end portion including the imaging section and the illumination section. The end of the insert section needs not to be the entire configuration of the imaging section 200 or a light source section 600 illustrated in FIG. 6. The imaging section disposed in the end portion of the insert section only needs to include at least a configuration for receiving light from an object. For example, a lens system 110 illustrated in FIG. 6 may be disposed in the end portion of the insert section with an image sensor 250 and the like disposed outside the end portion. A configuration of the illumination section for irradiating the object with the illumination light may only be disposed in the end portion of the insert section. For example, a light guide section 120 illustrated in FIG. 6 may be disposed in the end portion of the insert section with the light source section 600 disposed outside the end portion.

In the description below, a system configuration example of a focus control device according to the present embodiment will be described first, and a flow of the AF control will be then described in detail. The description is given below with the entire endoscope system including the focus control device as an example.

2. System Configuration Example

An endoscope system according to the present embodiment is described below with reference to FIG. 6. The endoscope system according to the present embodiment includes the rigid scope 100 that is inserted into a body, the imaging section 200 (image sensor) that is connected to the rigid scope 100, the processing section 300 (processor), a display section 400 (display), an external I/F section 500, and the light source section 600.

The light source section 600 includes a white light source 610 that emits white light, and a light guide cable 620 that guides the light emitted from the white light source 610 to the rigid scope.

The rigid scope 100 includes the lens system 110 that includes an objective lens, a relay lens, an eyepiece, and the like, and the light guide section 120 that guides the light emitted from the light guide cable 620 to the end of the rigid scope.

The imaging section 200 includes an imaging lens system 240 that forms an image of the light emitted from the lens system 110. The imaging lens system 240 includes a focus lens 220 that adjusts an in-focus object plane position. The imaging section 200 also includes the image sensor 250 that photoelectrically converts the reflected light focused by the imaging lens system 240 to generate an image, a focus lens driver section 230 that drives the focus lens 220, and an AF start/stop button 210 that controls AF start/stop.

For example, the image sensor 250 is a primary color Bayer image sensor in which any one of R, G, and B color filters are disposed in a Bayer array. The image sensor 250 may be any other image sensors such as an image sensor that utilizes a complementary color filter, a stacked image sensor that is designed so that each pixel can receive light having a different wavelength without utilizing a color filter, and a monochrome image sensor that does not utilize a color filter, as long as the object can be captured to obtain an image. The focus lens driver section 230 is implemented by any actuator such as a voice coil motor (VCM), for example.

The processing section 300 includes an A/D conversion section 310, a pre-processing section 320, an image processing section 330, the AF control section 340, and a control section 350. The A/D conversion section 310 converts analog signals sequentially output from the image sensor 250 into a digital image, and sequentially outputs the digital image to the pre-processing section 320. The pre-processing section 320 performs image processing (e.g., white balance process and interpolation process (demosaicing process)) on the image output from the A/D conversion section 310, and sequentially outputs the resulting image to the image processing section 330 and the AF control section 340. The AF control section 340 is described in detail below. The image processing section 330 performs image processing such as color conversion process, grayscale transformation process, edge enhancement process, scaling process, and noise reduction process on the image output from the pre-processing section 320, and sequentially outputs the resulting image to the display section 400. The display section 400 is a liquid crystal monitor, for example. The display section 400 displays the image sequentially output from the image processing section 330.

The control section 350 is bidirectionally connected to the external I/F section 500, the image processing section 330, the AF control section 340, the image sensor 250, the AF start/stop button 210 and the light source section 600, and exchanges a control signal with these components. The external I/F section 500 is an interface that allows the user to perform an input operation on the endoscope system, for example. The external I/F section 500 includes a setting button for setting the position and the size of the AF area, an adjustment button for adjusting the image processing parameters, and the like.

3. Detail of AF Control

Next, an overview of the AF control performed by the AF control section 340 according to the present embodiment is described with reference to FIG. 7. When the user has operated the AF start/stop button 210 to start the AF process, the AF control section 340 starts a focus operation. When the focus operation starts, the AF control section 340 causes the focus lens 220 to make a wobbling motion in synchronization with the acquisition timing of the image that is sequentially output from the A/D conversion section 310, through a known technique. Then, the AF control section 340 determines the in-focus direction based on the images acquired during the wobbling motion (S100). The in-focus direction determination (S100) is described in detail below. Then, the AF control section 340 changes the wobbling center position based on the in-focus direction determined by the step S100 (S110). The in-focus direction determined in S100 is any one of "NEAR" and "FAR" as described below. Specifically, when the in-focus direction is determined to be "NEAR", the AF control section 340 moves the wobbling center position by a given amount in a direction in which an in-focus object plane position moves toward a near side to be closer to the image sensor 250. On the other hand, when the in-focus direction is determined to be "FAR", the AF control section 340 moves the wobbling center position by a given amount in a direction in which an in-focus object plane position moves toward an infinite side to be farther from the image sensor 250.

The AF control section 340 determines whether or not the object has been brought into focus (S120). The AF control section 340 may determine whether or not the object has been brought into focus by performing a known in-focus determination process or the like. When the AF control section 340 has determined that the object has not been brought into focus, the AF control section 340 repeats the steps S100 to S120 to gradually bring the wobbling center position closer to the in-focus position. When the AF control section 340 has determined that the object has been brought into focus, the AF control section 340 stops causing the focus lens 220 to make a wobbling motion, and terminates the focus operation.

When the AF control section 340 has terminated the focus operation, the AF control section 340 starts a standby operation. Specifically, when the standby operation starts, the AF control section 340 detects a change in scene (S130). The AF control section 340 detects a change in scene by monitoring a change in the color or the brightness of an image, the motion of an image, and the like using the image sequentially output from the pre-processing section 320, for example. The AF control section 340 determines whether or not a change in scene has been detected (S140). When a change in scene has not been detected, the AF control section 340 performs the step S130 again. When a change in scene has been detected, the AF control section 340 terminates the standby operation. When the AF control section 340 has terminated the standby operation, the AF control section 340 resumes the focus operation. Note that the AF control section 340 fixes the focus lens 220 at a position when the focus operation has been terminated and does not drive the focus lens 220 during the standby operation, for example.

Figure 8:
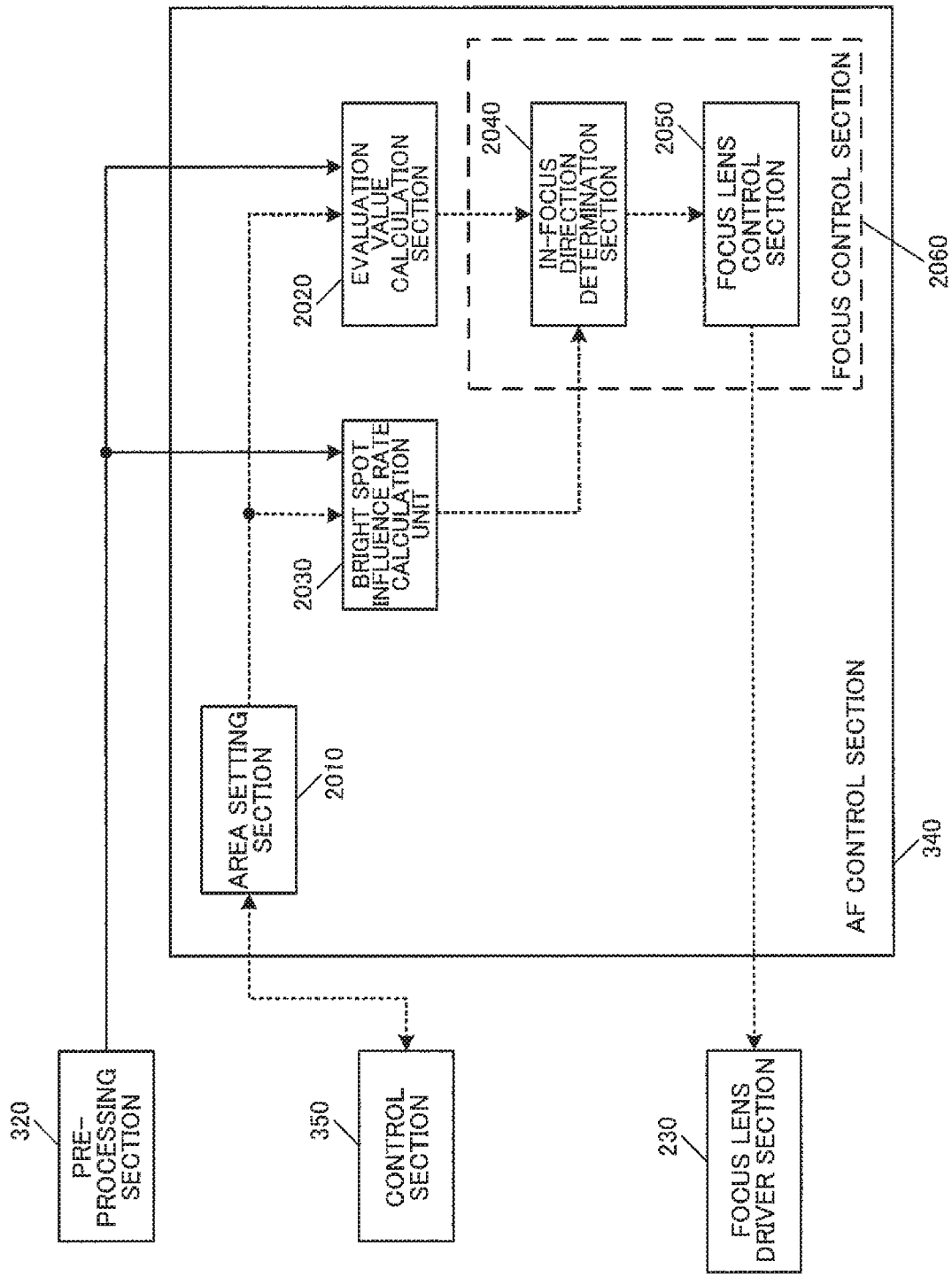
FIG. 8 illustrates a configuration example of an AF control section.
Figure 9:
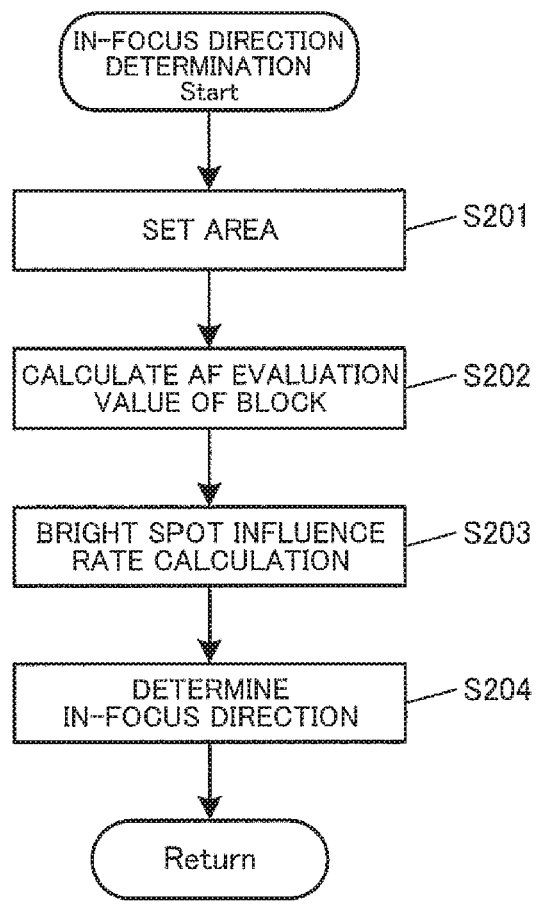
FIG. 9 is a flowchart illustrating in-focus direction determination processing.

The in-focus direction determination (S100) performed by the AF control section 340 is described in detail with reference to FIG. 8 and FIG. 9. For example, the AF control section 340 includes the area setting section (AF area setting section) 2010, the evaluation value calculation section (block AF evaluation value calculation section) 2020, the bright spot influence rate calculation section 2030, the in-focus direction determination section 2040, and the focus lens control section 2050.

Figure 10:
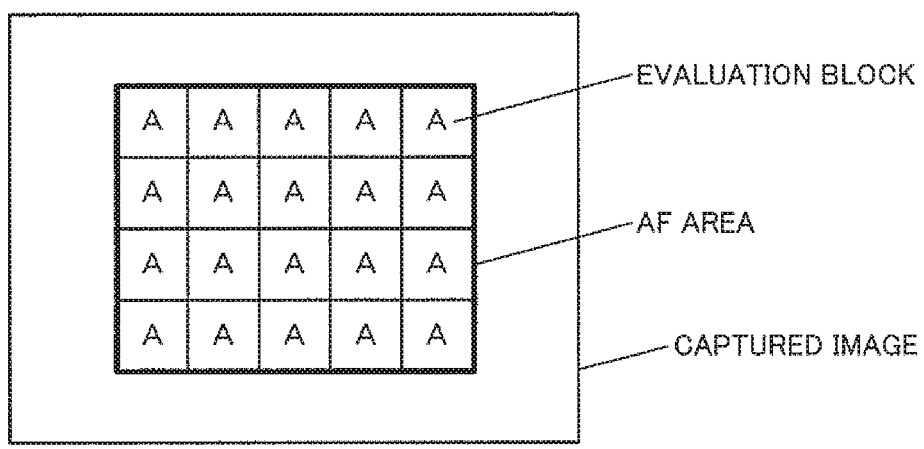
FIG. 10 illustrates an example of an AF area and an evaluation block set on a captured image.

First of all, the area setting section 2010 sets an AF area, including a plurality of blocks on an image, based on information such as a position, a size, and the like of the AF area output from the control section 350 (S201). FIG. 10 illustrates an example of the AF area thus set. A rectangle as an outer circumference illustrated in FIG. 10 represents the entire image, and a rectangle with a sign A represents the evaluation block as an area in which the AF evaluation value and the bright spot influence rate are calculated as described below. In FIG. 10, the AF area is an area surrounding the entire evaluation blocks. In FIG. 10, total of 20 evaluation blocks (five in the horizontal direction×four in the vertical direction) are set at a center portion of the image. The number and the size of the evaluation blocks may be changed as appropriate in accordance with an object, a user operation, and the like. The evaluation blocks do not necessarily need to be contiguous, meaning that the blocks may be sparsely set. The area setting section 2010 outputs setting information on the AF area to the evaluation value calculation section 2020 and the bright spot influence rate calculation section 2030.

The evaluation value calculation section 2020 calculates an AF evaluation value of each evaluation block from the pixel value of the image output from the pre-processing section 320 and the AF area information output from the area setting section 2010 (S202). The AF evaluation value increases as the degree of in-focus to the object in the evaluation block increases, and is calculated based on frequency characteristics, luminance distribution characteristic, and the like of the image. For example, the AF evaluation value is a result of accumulating output values obtained with a high pass filter or a band pass filter to the pixels in the evaluation block. The AF evaluation value may further be a distribution range, distribution, standard deviation, or the like of a luminance histogram as one example of luminance distribution characteristics calculated from the pixels in the evaluation block. The evaluation value calculation section 2020 outputs the AF evaluation value in each evaluation block thus calculated to the in-focus direction determination section 2040.

The bright spot influence rate calculation section 2030 calculates the bright spot influence rate in each evaluation block, based on the pixel value of the image output from the pre-processing section 320 and the AF area information output from the area setting section 2010 (S203). The bright spot influence rate is a value indicating a degree of negative impact of a bright spot on the AF control.

Next, how bright spot influence rate is calculated will be described. First of all, the bright spot influence rate calculation section 2030 calculates a luminance signal using known conversion processing and the like from pixel values of R, G, and B channels of each pixel in the evaluation block. Then, the bright spot influence rate calculation section 2030 executes threshold value processing, using a given threshold value corresponding to a luminance value of a saturated pixel, on the luminance value of the luminance signal thus calculated, and determines whether or not each pixel is a high luminance pixel. Then, the determination results on all the pixels in the evaluation block are stored in an unillustrated memory as high luminance pixel determination results (high luminance pixel information). Here, for example, the high luminance pixel determination result may be 1 when the luminance value is equal to or higher than the threshold value, and the high luminance pixel determination result may be 0 when the luminance value is smaller than the threshold value. Next, the bright spot influence rate calculation section 2030 executes mask processing, using a bright spot influence rate calculation mask (mask information) on all the pixels in the evaluation block, to calculate the bright spot influence rate.

Figure 11A:
FIG. 11A illustrates an example of mask information and FIG. 11B illustrates an example of high luminance pixel information.
Figure 11B:

The bright spot influence rate calculation mask herein is a 5 pixel×5 pixel mask with the target pixel at the center as illustrated in FIG. 11A. In the mask processing, the bright spot influence rate calculation section 2030 first extracts the high luminance pixel determination results in a range that is the same as that of the bright spot influence rate calculation mask as illustrated in FIG. 11B. Then, the bright spot influence rate calculation section 2030 determines whether or not the high luminance pixel determination result is 1 for each of the pixels with a bright spot influence rate calculation mask value of 1, to determine an output value. The output value of the mask processing on the target pixel is set to be 1 when the high luminance pixel determination results of all the pixels with the bright spot influence rate calculation mask value of 1 are 1, and is otherwise set to be 0. Then, the bright spot influence rate calculation section 2030 calculates the sum of the output values obtained for all the pixels in the evaluation block, as the bright spot influence rate in the evaluation block. Then, the bright spot influence rate calculation section 2030 outputs the bright spot influence rate in each evaluation block thus calculated to the in-focus direction determination section 2040.

Through this processing, the bright spot influence rate calculation section 2030 can detect whether or not there is a high luminance portion having a size that is equal to or larger than the given size corresponding to an area set as 1 with the bright spot influence rate calculation mask. Contrast information on the tissue is lost in the high luminance portion. Thus, the AF evaluation value of an evaluation block becomes more difficult to accurately calculate as the area of the high luminance portion increases. The bright spot influence rate is a value corresponding to the area of the high luminance portion having a size that is equal to or larger than the given size in the evaluation block, and thus can also be used as an index for estimating an impact of such a phenomenon. When the evaluation block includes a plurality of high luminance portions having sizes that are equal to or larger than the given size, the bright spot influence rate is a value corresponding to the sum of the areas of the plurality of high luminance portions.

In FIG. 11A, the 5 pixel×5 pixel mask is used. Still, the given size corresponds to the pixels with the value of 1 in the mask information. For example, while the 5 pixel×5 pixel mask information is used in FIG. 11A, whether or not there is a high luminance portion with a value of 1 having a size of 3 pixel×3 pixel or larger is determined in the processing.

Here, the high luminance pixel determination is performed by using luminance values of pixels in an evaluation block. Alternatively, any one of or all of the pixel values of the R, G, and B channels may be used for performing the high luminance pixel determination. It is a matter of course that the bright spot influence rate calculation mask can be set to have any size and value.

Whether or not there is a high luminance portion having a size that is equal to or larger than a given size may be determined through processing other than the mask processing. For example, the bright spot influence rate may be calculated with the high luminance portion detected through known labeling processing or the like executed on the high luminance pixel determination result. In such a case, for example, a feature quantity such as an area, a circumference length, and a main shaft length from a group of pixels labeled as the high luminance portion is calculated. Then, the bright spot influence rate may be determined, with whether or not there is a high luminance portion having a size that is equal to or larger than the given size detected based on the feature quantity.

Then, the in-focus direction determination section 2040 determines the in-focus direction based on the AF evaluation value of each evaluation block output from the evaluation value calculation section 2020 and the bright spot influence rate in each evaluation block output from the bright spot influence rate calculation section 2030 (S204). More specifically, the in-focus direction determination section 2040 first determines whether or not each evaluation block is a null block, based on the bright spot influence rate of the evaluation block.

Here, for example, an evaluation block with a bright spot influence rate of a value other than 0 may be determined to be the null block. Such a configuration involves processing of setting all the blocks including the high luminance portion having a size that is equal to or larger than a given size to be the null blocks.

Alternatively, the bright spot influence rate may be compared with a given threshold value larger than 0, and an evaluation block with the bright spot influence rate that is equal to or larger than the threshold value may be set as the null block. Such a configuration involves processing of setting as the null block, a block, in which an area of the high luminance portion, having a size that is equal to or larger than the given size, has an area that is equal to or larger than the threshold value. When the bright spot influence rate calculation mask described above is used, the bright spot influence rate is calculated as an integer value. Thus, when the threshold value is equal to or smaller than 1, the processing described above can be regarded as processing of setting the evaluation block with the bright spot influence rate of a value other than 0 as the null block.

Next, the in-focus direction determination section 2040 sequentially stores the AF evaluation value of each evaluation block and the null block information in an unillustrated memory.

Then, for example, the in-focus direction determination section 2040 sets the evaluation block that has not been set to be the null block to be an effective block for each of images respectively obtained with the focus lens 220 moved in a NEAR direction and in a FAR direction as a result of the wobbling motion. Here, the evaluation block that has not been set as the null block may be set to be the effective block for both of the images obtained with the focus lens 220 respectively moved in the NEAR direction and in the FAR direction. The NEAR direction is a direction in which the in-focus object plane position moves toward the near side to be closer to the image sensor 250. The FAR direction is a direction in which the in-focus object plane position moves toward the infinite side to be farther from the image sensor 250. Then, the in-focus direction determination section 2040 calculates a NEAR side AF evaluation value as the sum of AF evaluation values of the effective blocks, in the AF evaluation values of the evaluation blocks corresponding to the image obtained with the focus lens 220 moved in the NEAR direction. Similarly, a FAR side AF evaluation value is calculated as the sum of AF evaluation values of the effective blocks, in the AF evaluation values of the evaluation blocks corresponding to the image obtained with the focus lens 220 moved in the FAR direction. Then, the in-focus direction determination section 2040 compares the NEAR side AF evaluation value and the FAR side AF evaluation value with each other, and sets the in-focus direction to be "NEAR" when the NEAR side AF evaluation value is larger, and otherwise sets the in-focus direction to be "FAR". Then, the in-focus direction determination section 2040 outputs the in-focus direction thus determined to be the focus lens control section 2050.

The in-focus direction determination section 2040 may determine the in-focus direction with the following method instead of the method described above.

Figure 12:
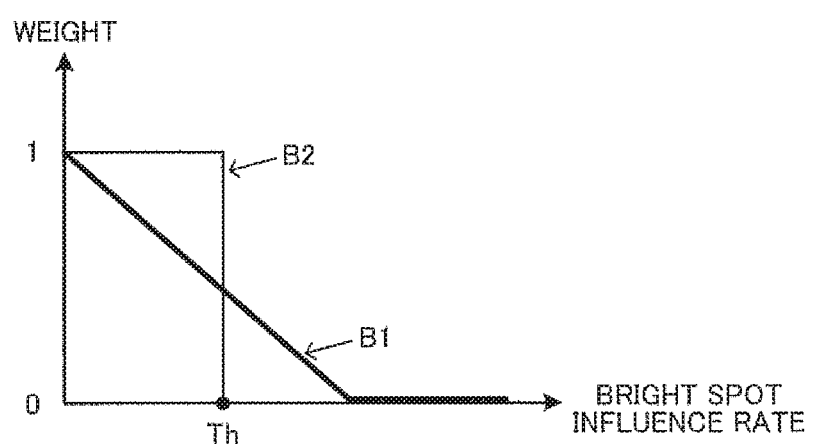
FIG. 12 is a diagram illustrating a relationship between a bright spot influence rate and weight information.

In the method, the in-focus direction determination section 2040 sets a weight of each evaluation block based on the bright spot influence rate of the evaluation block. In this process, the weight is set to be 1 when the bright spot influence rate is 0, decreases as the bright spot influence rate increases, and is set to be 0 when the bright spot influence rate is equal to or larger than a given value, as indicted by B1 in FIG. 12. B1 in FIG. 12 represents an example where the weight linearly changes. It is a matter of course that other settings can be employed.

The example of setting the null block described above can be regarded as an act of setting the weight in such a manner that the weight of the null block is set to 0 and that the weight of other blocks is set to 1. B2 in FIG. 12 represents a weight under this condition. Specifically, a given threshold value is set to the bright spot influence rate, and the weight is set to be 0 when the bright spot influence rate is equal to or larger than the threshold value, and is set to be 1 when the bright spot influence rate is smaller than the threshold value. It is a matter of course that the processing of setting all the blocks including the high luminance portion equal to or larger than the given size as the null blocks can be implemented with the threshold value set to a value close to 0 as described above (equal to or smaller than 1 when the bright spot influence rate is an integer value as described above).

Then, the in-focus direction determination section 2040 sequentially stores the AF evaluation value and the weight information set as described above of each evaluation block in an unillustrated memory. Then, the in-focus direction determination section 2040 performs weighted summing of the AF evaluation values of the evaluation blocks corresponding to the image obtained with the focus lens 220 moved in the NEAR direction based on the weight information thus stored. The resulting sum is obtained as the NEAR side AF evaluation value. Similarly, weighted summing of the AF evaluation values of the evaluation blocks corresponding to the image obtained with the focus lens 220 moved in the FAR direction is performed based on the weight information thus stored. The resulting sum is obtained as the FAR side AF evaluation value. Then, the in-focus direction determination section 2040 compares the NEAR side AF evaluation value and the FAR side AF evaluation value with each other, and may set the in-focus direction to be "NEAR" when the NEAR side AF evaluation value is larger, and may otherwise set the in-focus direction to be "FAR".

Figure 7:
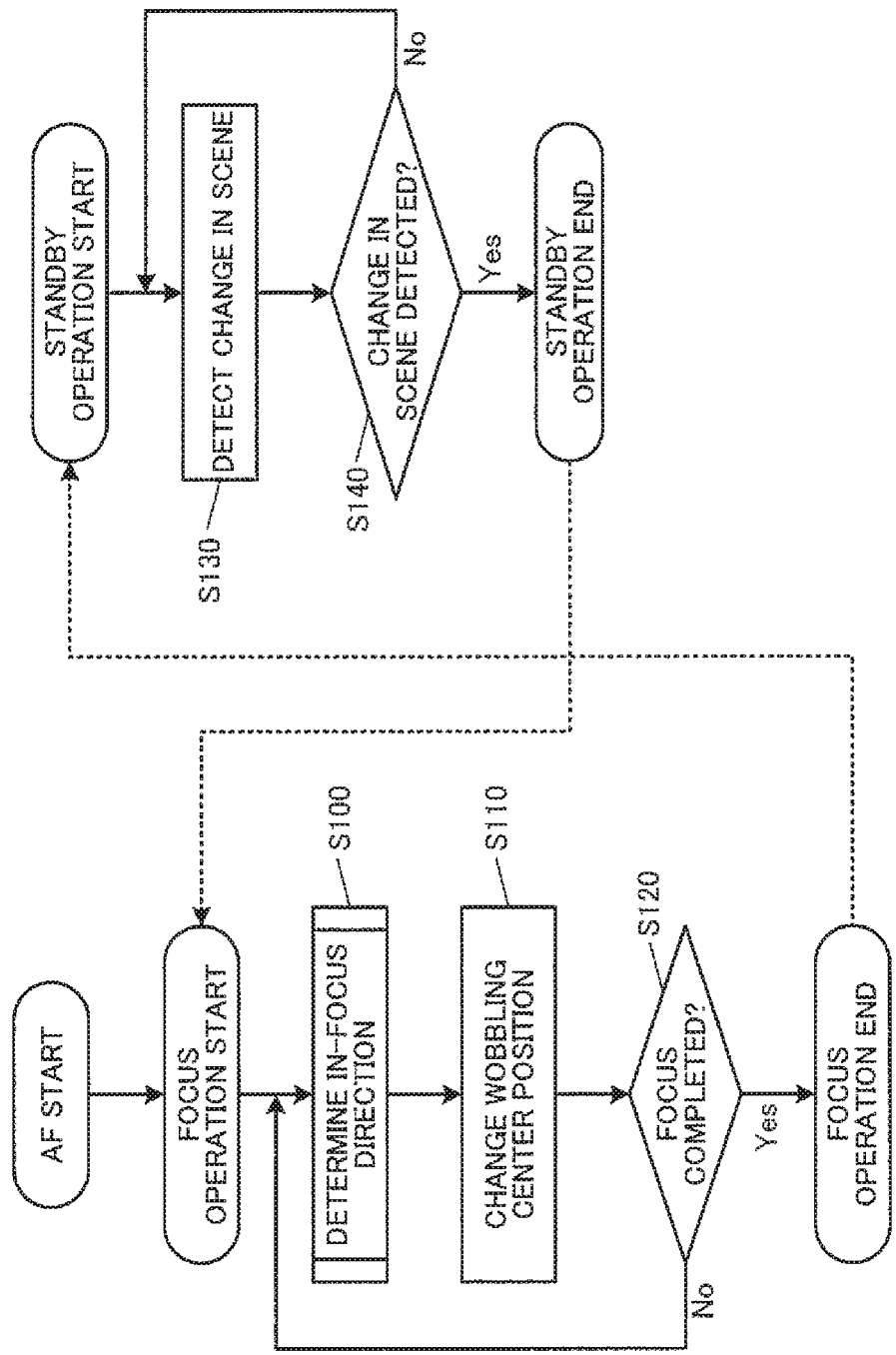
FIG. 7 is a flowchart illustrating a flow of AF control according to the present embodiment.

Finally, the focus lens control section 2050 changes the wobbling center position based on the in-focus direction thus determined, as in S110 in FIG. 7 described above.

Through this processing according to the present embodiment, the AF control with which the object can be accurately brought into focus can be implemented even when an image includes multiple high luminance portions of different sizes, with only the evaluation block including the bright spot having a negative impact on the AF control detected and the impact reduced.

The description in the present embodiment is directed to moving image AF employing a wobbling system. The present embodiment may also be applied to AF control for a hill-climbing system performed as in JP-A-2004-294788 and JP-A-8-321985, with the evaluation block including the bright spot having a negative impact on the AF control detected through the method described above.

As described above, the bright spot influence rate calculation section 2030 of the focus control device according to the present embodiment sets the bright spot influence rate to be high for a block including the high luminance portion determined to have a size equal to or larger than the given size, and does not set the bright spot influence rate to be high for a block including the high luminance portion determined to have a size smaller than the given size.

Thus, the impact of the high luminance portion with a large size (estimated to have a high intensity according to the present embodiment) that affects the AF control can be set to be high. The impact of the high luminance portion with a small size (estimated to have a low intensity according to the present embodiment) that does not affect the AF control can be set to be low. All things considered, the high luminance portions can be treated differently in accordance with their impact on the AF control.

The bright spot influence rate calculation section 2030 may obtain high luminance pixel information representing the high luminance pixels based on processing of comparing a pixel value of each pixel in the area (evaluation block) and a given pixel threshold value with each other, and determine whether or not there is the high luminance portion equal to or larger than the given size based on mask information corresponding to the given size and the high luminance pixel information.

The high luminance pixel information corresponds to FIG. 11B and the mask information corresponds to FIG. 11A. Thus, whether or not there is high luminance portion having a size that is equal to or larger than the given size can be determined by using the mask information. With the example illustrated in FIG. 11A and FIG. 11B, a simple AND operation may be performed for the number of times corresponding to the number of pixels in an evaluation block to determine whether or not an output value is equal to or larger than 1. Thus, there is an advantage that a processing load is small.

The bright spot influence rate calculation section 2030 may obtain the high luminance pixel information representing the high luminance pixel based on processing of comparing a pixel value of each pixel in the area and a given pixel threshold value with each other, and identify a group of the high luminance pixels that are contiguous as the high luminance portion based on the high luminance pixel information. Then, whether or not the high luminance portion has a size that is equal to or larger than the given size may be determined based on geometrical characteristics (size feature quantity) of the identified high luminance portion.

This configuration corresponds to the labeling processing (or clustering processing) described above. Specifically, when the information as illustrated in FIG. 11B is acquired, a cluster including the pixel with an output value of 1 is determined, and a group of high luminance pixels provided with the same label (high luminance pixels classified into the same cluster) are identified as a single high luminance portion. Such a configuration can obtain a size (such as a diameter, a main shaft length, a circumference length, and an area) through geometrical processing because the specific shape of the high luminance portion thus identified is recognizable. With the result of such processing, whether or not the high luminance portion has a size that is equal to or larger than the given size can be easily determined.

When a high luminance portion has a size that is equal to or larger than the given size is detected in an area, the bright spot influence rate calculation section 2030 may calculate a value corresponding to an area of the high luminance portion thus detected as the bright spot influence rate.

Thus, the value corresponding to the area of the high luminance portion having a size that is equal to or larger than the given size can be obtained as the bright spot influence rate. In the example where the mask information is used as illustrated in FIG. 11A and FIG. 11B, the bright spot influence rate corresponds to the number of times 1 is output (the number of processing target pixels). A high luminance portion with a larger area is more likely to include a high luminance portion of a given size corresponding to the mask information. Thus, the bright spot influence rate is information on an area. A high luminance portion that is smaller than the given size is also an area with a certain area, but does not provide an output value of 1 in the mask processing. Thus, the high luminance portion that is smaller than the given size does not contribute to the bright spot influence rate. A high luminance portion with a larger area leads to a larger lost amount of structures (contrasts) in the high luminance portion, which are supposed to be in a captured image. Thus, the value corresponding to an area can be used as information representing a magnitude of impact of the bright spot. In the configuration employing the labeling processing, for example, the number of high luminance pixel provided with the same label may be obtained as the area of the high luminance portion.

When a plurality of high luminance portions having sizes that are equal to or larger than the given size are detected in an area, the bright spot influence rate calculation section 2030 may calculate a value corresponding to the sum of areas of the plurality of high luminance portions thus detected as the bright spot influence rate.

A plurality of high luminance portions having sizes that are equal to or larger than the given size, each having negative impact on AF, have a larger negative impact on AF compared with a single high luminance portion having a size that is equal to or larger than the given size. Thus, the bright spot influence rate may be a value corresponding to the sum of the areas of the high luminance portions having sizes that are equal to or larger than the given size in an area, to reflect the difference in the negative impact.

The focus control section 2060 (more specifically, the in-focus direction determination section 2040) sets an area with the bright spot influence rate having a size that is equal to or larger than the given threshold value to be a null area (null block), and may perform the focus control based on the AF evaluation values of areas other than the null areas.

Thus, the focus control involves no information on the area determined to have a large bright spot influence rate, whereby accurate focus control can be achieved. For example, in the processing of determining the driving direction of the focus lens 220 by comparing the NEAR side AF evaluation value (the sum of the AF evaluation values of the evaluation blocks in a NEAR side captured image) and the FAR side AF evaluation value (the sum of the AF evaluation values of the evaluation blocks in a FAR side captured image) with each other, the sum does not include the AF evaluation values of the evaluation blocks set to be the null blocks. All things considered, information on the evaluation block with a bright spot having a large impact can be prevented from being used in the AF control.

A given evaluation block set to be the null block on the NEAR side may not be set to be the null block on the FAR side or vice versa. Thus, a block evaluated differently between NEAR and FAR as described above may be set to be the effective block on a side where the block has not been set to be the null block (to contribute to the sum), or set to be the null block also on the side where the block has not been set to be the null block. Note that the former scenario might result in a difference in the number of effective blocks between the NEAR side and the FAR side. Thus, a modification may be employed in which the NEAR side AF evaluation value and the FAR side AF evaluation value are each an average value of each effective block or the other like values, instead of being a simple sum.

The focus control section 2060 may set weight information that decreases as the bright spot influence rate increases to each of a plurality of areas, and may perform the focus control based on the AF evaluation value weighted based on the weight information.

B1 in FIG. 12 described above represents one example of the weight information the decreases as the bright spot influence rate increases. With such a configuration, the AF evaluation value of a given area can be flexibly used instead of having only two choices of being used or completely omitted in the focus control.

The focus control device and the like according to the present embodiment may include a processor and a memory. For example, functions of sections of the processors may each be implemented with individual hardware, or may be implemented with integrated hardware. For example, the processor may include hardware that may include at least one of a circuit that processes a digital signal and a circuit that processes an analog signal. For example, the processor may include one or a plurality of circuit devices (such as ICs) or one or a plurality of circuit elements (for example, a resistor, a capacitor, and the like) mounted on a circuit board. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an application-specific integrated circuit (ASIC). The processor may include an amplifier circuit, filter circuit, and the like that process an analog signal. The memory may be a semiconductor memory (e.g., SRAM or DRAM), a register, a magnetic storage device such as a hard disk device, or an optical storage device such as an optical disk device. For example, the memory stores a computer-readable instruction. A function of each section of the focus control device and the like is implemented by causing the processor to execute the instruction. The instruction may be an instruction included in an instruction set that is included in a program, or may be an instruction that causes a hardware circuit included in the processor to operate.

Although the present embodiment has been described in detail above, those skilled in the art will readily appreciate that many modifications are possible in the embodiments without materially departing from the novel teachings and advantages of the invention. Accordingly, all such modifications are intended to be included within scope of the invention. Any term cited with a different term having a broader meaning or the same meaning at least once in the specification and the drawings can be replaced by the different term in any place in the specification and the drawings. The configurations and the operations of the focus control device, the imaging device, and the like are not limited to those described above in connection with the embodiments. Various modifications and variations may be made of those described above in connection with the embodiments.

What is claimed is:

1. A focus control device comprising:
a processor comprising hardware, wherein the processor is configured to:
for each of a plurality of areas, the each of the plurality of areas including a plurality of pixels, on a captured image acquired by an image sensor:
calculate an autofocus (AF) evaluation value for the each of the plurality of areas;
determine whether a plurality of high luminance portions exists within the each of the plurality of areas, wherein each of the plurality of high luminance portions is a group of contiguous pixels having a luminance value equal to or larger than a given luminance value;
in a case where the plurality of high luminance portions is determined to exist within the each of the plurality of areas, determine whether one or more of the plurality of high luminance portions has a size equal to or larger than a given size;
set a value of a bright spot influence rate for the each of the plurality of areas including one or more of the plurality of high luminance portions having a size equal to or larger than the given size to a high value equal to or higher than a threshold value; and
set the value of the bright spot influence rate for the each of the plurality of areas not including one or more of the plurality of high luminance portions having the size equal to or larger than the given size to a low value lower than the threshold value; and
perform focus control based on the AF evaluation value and whether the bright spot influence rate is the high value or the low value of the plurality of areas.

2. The focus control device according to claim 1, wherein the processor is configured to determine whether or not one or more of the plurality of high luminance portions has a size that is equal to or larger than the given size based on mask information corresponding to the given size.

3. The focus control device according to claim 1, wherein the processor is configured to determine whether or not one or more of the plurality of high luminance portions has a size that is equal to or larger than the given size based on geometric characteristics of the one or more high luminance portions.

4. The focus control device according to claim 1, wherein the processor is configured to set the value of the bright spot influence rate for the each of the plurality of areas including one of the plurality of high luminance portions having the size equal to or larger than the given size to a high value corresponding to an area of the one of the plurality of high luminance portions.

5. The focus control device according to claim 1, wherein the processor is configured to set the value of the bright spot influence rate for the each of the plurality of areas including more than one of the plurality of high luminance portions having the size equal to or larger than the given size to a high value corresponding to a sum of areas of the more than one of the plurality of high luminance portions having the size equal to or larger than the given size.

6. The focus control device according to claim 1, wherein the processor is configured to:
set each of the plurality of areas with the bright spot influence rate having the high value to be a null area, and
perform the focus control based on the AF evaluation value of one or more of the plurality of areas other than the each of the plurality of areas set to be the null area.

7. The focus control device according to claim 1, wherein the processor is configured to:
set weight information that decreases as the bright spot influence rate increases to each of the plurality of the areas; and areas, and
perform the focus control based on the AF evaluation value weighted based on the weight information.

8. An imaging device comprising:
the focus control device according to claim 1; and
the image sensor.

9. An endoscope system comprising:
the focus control device according to claim 1; and
an insert section configured to be inserted into an observation target,
wherein the insert section comprises:
a light source configured to emit illumination light; and
the image sensor, wherein the image sensor is configured to acquire the captured image based on reflected light from an object illuminated by the illumination light.

10. A method comprising:
for each of a plurality of areas, the each of the plurality of areas including a plurality of pixels, on a captured image acquired by an image sensor:
calculating an autofocus (AF) evaluation value for the each of the plurality of areas;
determining whether a plurality of high luminance portions exists within the each of the plurality of areas, wherein each of the plurality of high luminance portions is a group of contiguous pixels having a luminance value equal to or larger than a given luminance value;
in a case where the plurality of high luminance portions is determined to exist within the each of the plurality of areas, determining whether one or more of the plurality of high luminance portions has a size equal to or larger than a given size;
setting a value of a bright spot influence rate for the each of the plurality of areas including one or more of the plurality of high luminance portions having a size equal to or larger than the given size to a high value equal to or higher than a threshold value; and setting the value of the bright spot influence rate for the each of the plurality of areas not including one or more of the plurality of high luminance portions having the size equal to or larger than the given size to a low value lower than the threshold value; and performing focus control based on the AF evaluation value and whether the bright spot influence rate is the high value or the low value of the plurality of areas.

\* \* \* \* \*